United States Patent
Nichols et al.

(10) Patent No.: US 7,323,207 B2
(45) Date of Patent: Jan. 29, 2008

(54) METHOD AND APPARATUS FOR FINGERPRINT DETECTION

(75) Inventors: Walter A. Nichols, Chesterfield, VA (US); Daniel Diefenbach, Richmond, VA (US)

(73) Assignee: Philip Morris USA Inc., Richmond, VA (US)

( * ) Notice: Subject to any disclaimer, the term of this patent is extended or adjusted under 35 U.S.C. 154(b) by 242 days.

(21) Appl. No.: 10/532,122

(22) PCT Filed: Oct. 21, 2003

(86) PCT No.: PCT/US03/33145

§ 371 (c)(1),
(2), (4) Date: Jun. 24, 2005

(87) PCT Pub. No.: WO2004/038640

PCT Pub. Date: May 6, 2004

(65) Prior Publication Data

US 2005/0252444 A1 Nov. 17, 2005

Related U.S. Application Data

(60) Provisional application No. 60/419,567, filed on Oct. 21, 2002.

(51) Int. Cl.
*B05D 7/00* (2006.01)
*B05C 5/02* (2006.01)

(52) U.S. Cl. .................. 427/1; 427/248.1; 118/31.5; 118/715; 392/386; 392/390; 392/398; 392/404; 239/136

(58) Field of Classification Search ............ 118/31.5, 118/715; 427/1, 248.1; 392/386, 390, 398, 392/404; 239/136, 135
See application file for complete search history.

(56) References Cited

U.S. PATENT DOCUMENTS

| | | | |
|---|---|---|---|
| 4,258,073 A | | 3/1981 | Payne |
| 4,260,873 A | * | 4/1981 | Simmonds ............ 392/404 |
| 4,294,383 A | | 10/1981 | Hession et al. |
| 4,297,383 A | | 10/1981 | Bourdon |
| 4,407,842 A | | 10/1983 | Shepard |
| 4,461,235 A | | 7/1984 | Morton |
| 4,550,041 A | | 10/1985 | Thompson et al. |
| 4,613,515 A | | 9/1986 | Reggio |
| 4,700,657 A | | 10/1987 | Butland |
| 4,749,778 A | | 6/1988 | Fukuzawa et al. |
| 4,837,260 A | | 6/1989 | Sato et al. |
| 5,342,645 A | | 8/1994 | Eisele et al. |
| 5,348,759 A | | 9/1994 | Weaver et al. |
| 5,395,445 A | | 3/1995 | Bohanan |
| 5,424,092 A | | 6/1995 | Weaver et al. |
| 5,462,597 A | | 10/1995 | Jubram |
| 5,465,765 A | | 11/1995 | Martindale |
| 5,559,923 A | * | 9/1996 | Robelen ............... 392/397 |
| 6,069,214 A | | 5/2000 | McCormick et al. |
| 6,069,219 A | | 5/2000 | McCormick et al. |
| 6,423,946 B1 | | 7/2002 | Berka et al. |

* cited by examiner

*Primary Examiner*—Laura Edwards
(74) *Attorney, Agent, or Firm*—Buchanan Ingersoll & Rooney PC

(57) ABSTRACT

A portable apparatus for detecting latent fingerprints that discharges a vapor of a cyanoacrylate-containing solution. The apparatus comprises a reservoir for holding a liquid solution comprising cyanoacrylate, a valve for controlling the release of the solution through a capillary flow passage, and a power supply for heating the capillary flow passage and vaporizing the solution. When cyanoacrylate vapor contacts latent fingerprints, the fingerprints are rendered visible.

19 Claims, 1 Drawing Sheet

METHOD AND APPARATUS FOR FINGERPRINT DETECTION

Figure 1:
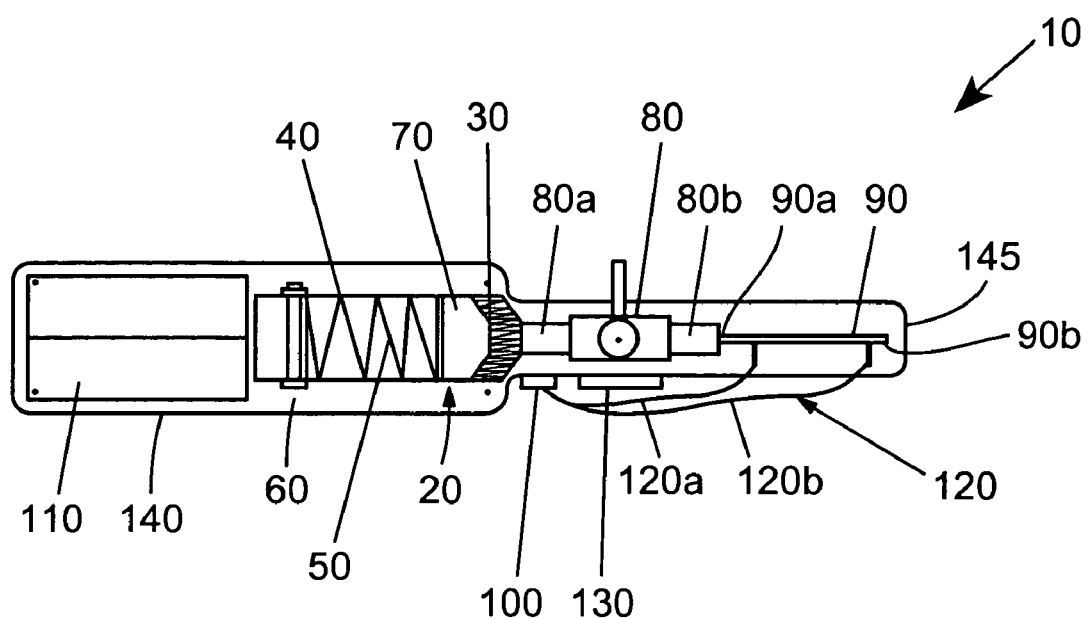

This application is a national stage application under 35 USC §371 of International Application Number PCT/US2003/033145, filed Oct. 21, 2003, the international Application being published in English. This application also claims priority under 35 USC §119 to U.S. Provisional Application No. 60/419,567, filed Oct. 21, 2002.

BACKGROUND

1. Field of the Invention

The present invention is directed generally to making latent fingerprints visible and semipermanent. More specifically, the present invention is related to a method and apparatus for vaporizing a liquid cyanoacrylate composition that polymerizes upon contact with the fingerprint.

2. Background Information

It is known that cyanoacrylate can be used to develop fingerprints through a polymerization reaction in which cyanoacrylate vapor contacts a latent fingerprint. Chemicals in the fingerprint cause the polymerization of the cyanoacrylate resulting in an enhanced visual image of the print.

U.S. Pat. Nos. 5,424,092; 5,348,759; 5,342,645; 4,613,515; 4,550,041; 4,461,235; and 4,407,842 relate to apparatus and methods for developing latent fingerprints using cyanoacrylate. U.S. Pat. Nos. 4,700,657; 4,461,235 and 4,294,383 disclose closed fingerprint detection systems using cyanoacrylate. U.S. Pat. Nos. 5,462,597 and 5,395,445 disclose methods for detecting fingerprints on skin.

The '092 and '759 patents, for example, disclose a housing containing a thermally stable porous material that is impregnated with a liquid cyanoacrylate, which is allowed to cure. A portable heating device such as a propane torch can be used to vaporize the cyanoacrylate, which is propelled toward the object to be tested by the torch exhaust.

The '515, '041 and '235 patents disclose a method and apparatus whereby vapors are generated from a thin film of a storage stable cyanoacrylate monomer composition that has been complexed to render the composition substantially non-flowable. An envelope package for the monomer composition may be peeled open to expose the inner surfaces coated with a film of the composition.

The methods and apparatus described above are slow to display the fingerprints and, in some instances, require that the target area be placed in a sealed container. Accordingly, there is a need for a portable, rapid, simple and safe method for rendering latent fingerprints detectable.

SUMMARY OF THE INVENTION

The invention relates to a fingerprint detection apparatus comprising (a) a liquid source containing a solution, such as a cyanoacrylate solution, which upon vaporization and contact with a surface to be inspected can provide an image of a fingerprint; (b) a flow passage in fluid communication with the liquid source; (c) a valve operable to control flow of liquid from the liquid source to the flow passage; (d) a heater arranged to heat the solution in the flow passage into a gaseous state; and (e) an optional switch operable to activate the valve and the heater such that solution flowing through the flow passage is vaporized and directed outwardly from the apparatus.

The flow passage preferably comprises a capillary tube, such as a metal tube, having a maximum diameter of 0.01 to 10 mm or the flow passage comprises a capillary sized opening of any configuration having a maximum width of 0.01 to 10 mm or transverse area of $8 \times 10^{-5}$ to 80 mm$^2$. The heater can comprise a section of the capillary tube which is heated by resistance heating thereof or the heater can comprise a layer of resistance heating material located along the flow passage.

The apparatus may include a receptacle for receiving the liquid source such as a replaceable cartridge. For delivery of the liquid, the liquid source can include a spring biased plunger operable to force liquid out of the liquid source.

The apparatus may further include a power supply, the switch being operable to open the valve and connect the power supply to the heater. The power supply may comprise at least one battery and a voltage regulator, the voltage regulator being operable to supply a selected voltage to the heater.

The cyanoacrylate solution may comprise a mixture of cyanoacrylate monomer and a solvent and may comprise 1 to 20% by volume of the cyanoacrylate monomer. The solution can also include a soluble fluorescent dye that can generate a fluorescent vapor that is directed at the surface to be inspected.

The invention also relates to a method of using the fingerprint detection apparatus comprising (a) flowing the solution through the flow passage while heating the flow passage with the heater; (b) forming a vapor by vaporizing the solution; and (c) directing the vapor onto a surface to be inspected.

The apparatus can be used as a portable hand held apparatus that can be held in a user's hand while directing the vapor at the surface to be inspected by using the switch to open the valve and activate the heater. The solution can be supplied to the flow passage by pressurizing the liquid source. Furthermore, the liquid source can comprise a replaceable cartridge containing a cyanoacrylate solution. An image of a latent fingerprint can be formed by allowing the vapor to react with organic compounds of the fingerprint.

BRIEF DESCRIPTION OF THE DRAWING FIGURES

Various features and advantages of the invention will become apparent from the following detailed description of preferred embodiments in connection with the accompanying drawing in which like numerals designate like elements and in which:

FIG. 1 is a cross-sectional view of an apparatus useful for carrying out a preferred method in accordance with the invention.

DETAILED DESCRIPTION OF THE PREFERRED EMBODIMENTS

Fingerprints can fall into one of several different classifications, e.g. visible, impression, and latent. Investigators typically seek to obtain a portable, permanent copy of a fingerprint, such as a photograph. Visible fingerprints can be photographed directly, and impression fingerprints can usually be photographed under special lighting conditions. Latent fingerprints, however, which are invisible to the eye, are difficult to photograph.

Cyanoacrylate fuming is a chemical technique for making latent fingerprints visible. Latent fingerprints are composed of several chemicals exuded through pores in the fingertips that are left on objects which are touched. The primary component of latent fingerprints is water, which will evaporate after a fairly short period of time. The solid components of latent fingerprints, however, can remain on a surface for a much longer period of time. These other components include organic compounds like amino acids, glucose, lactic acid, peptides, ammonia, riboflavin, and isoagglutinogens as well as inorganic chemicals like potassium, sodium, carbon trioxide, and chlorine.

Cyanoacrylates can react with the moisture in the air and the traces of amino acids, fatty acids, and proteins in a latent fingerprint to produce a visible, sticky white material that forms along the ridges of the fingerprint and visually enhances the fingerprint. Exposure of gaseous cyanoacrylate to the fingerprint in the presence of atmospheric humidity can trigger the reaction. When cyanoacrylate monomer contacts the fingerprint, it can polymerize by anionic vinyl polymerization, which is a type of vinyl polymerization that is begun in the presence of an initiator. Water from the air or trace amounts of moisture on the surface to be tested can serve as the initiator. The resulting image can be photographed directly or following further enhancement.

For example, after developing the fingerprint image by exposing the latent print to cyanoacrylate vapor, the image of the fingerprint may not be easy to photograph. The chemical deposits left by the reaction with the cyanoacrylate are white and may provide insufficient contrast for an effective photograph, particularly if the background surface is also white. To enhance imaging, different colored dusts, which will cling to the cyanoacrylate residue, may be brushed onto the image of the fingerprint.

Referring to FIG. 1, there is shown an exemplary apparatus 10 for rendering latent fingerprints detectable. The apparatus comprises a reservoir 20 that contains a volume of cyanoacrylate solution 30. A spring-loaded piston 40 or other suitable pressurizing arrangement maintains the solution in the reservoir under pressure. Upon loading of a reservoir 20 in the apparatus 10, spring 50 is compressed such that piston 40 provides a pressurizing force on movable plunger 70 of the reservoir. Thus, solution is removed from the reservoir 20 due to pressure of piston 40 on plunger 70. The apparatus includes valve 80, which provides fluid communication between the reservoir 20 and an inlet 90a of a capillary flow passage in the form of a capillary tube 90 via connections 80a and 80b. The outlet end of the capillary tube 90b is open to atmosphere. The capillary tube 90 is preferably made of stainless steel, but can be any electrically conductive material. Alternatively, the flow passage can be in a non-electrically conductive material and heated by a heater arrangement extending along the flow passage. The valve 80 is preferably activated by an on/off switch 130 which allows the user to control the flow of the solution from the reservoir into the flow passage.

The apparatus also comprises a voltage regulator 100. The use of the voltage regulator allows the apparatus to be made economically by obviating more expensive control circuitry. That is, the voltage regulator supplies stepped down power from a power source to the heated flow passage when the on/off switch 130 opens valve 80. The voltage regulator can be a 3-10 V in/2 V out regulator; however, persons with ordinary skill in the art will recognize that the input and output voltages of the voltage regulator can be selected to accommodate other parameters of the apparatus, such as the resistivity of the heater and/or the desired temperature of the flow passage during operation.

The input to the voltage regulator is connected to a battery pack 110, which supplies DC power to the voltage regulator. The battery pack can comprise, for example, four 1.2 V rechargeable Ni-MH "AA" batteries. The output to the voltage regulator is connected to connecting wires 120a, 120b via on/off switch 130, which is normally off. The connecting wires are, in turn, connected to spaced-apart locations along the capillary tube, preferably the anterior and posterior ends of the capillary tube 90a, 90b. When the switch 130 is turned "on" the voltage regulator supplies sufficient power to the capillary tube to cause resistance heating of the capillary tube and vaporization of the liquid supplied to the capillary tube.

Connecting wires 120a, 120b can be attached to the exterior of the capillary tube using any suitable electrical connection, such as solder, weld, braze or a mechanical connection such as a clamping arrangement. The application of a voltage across the connecting wires causes the temperature of the capillary tube between the connecting wires to increase due to resistance heating of the tube. It will be appreciated by those skilled in the art that the temperature of the capillary tube is a function of the distance, d, between the connecting wires, the resistivity and cross sectional area of the capillary tube, as well as the applied voltage. Thus, both the temperature and temperature distribution across the capillary tube can be adjusted to provide optimized vaporization of the cyanoacrylate solution as it passed through the capillary tube.

Advantageously, the heating of the capillary tube by the application of a constant voltage is nearly instantaneous. Likewise, the capillary tube cools very rapidly when the voltage is removed. Thus, there is very little incubation or heat-up time needed before the apparatus is ready for use.

In order to vaporize the cyanoacrylate solution, the capillary tube is preferably brought to a temperature above the boiling point ("bp") of the solution. For a cyanoacrylate (bp ~55° C.) and propylene carbonate (bp ~242° C.) solution, for example, the temperature of the capillary tube is from between about 240 to 270° C., preferably 250° C. Because liquid flows through the capillary tube while it is heated, the temperature of the capillary tube can be maintained in a desired temperature range.

The switch 130 activates valve 80 such that the valve opens when switch 130 is turned on when "on" and the valve closes when switch 130 is turned "off".

The apparatus can be enclosed in housing 140, which has an opening 145 at the distal end of the apparatus to allow the vaporized solution to exit the capillary tube and be applied to the object or surface to be tested. The housing 140 can be formed of any suitable material such as plastic or metal. The housing can keep hot surfaces of the apparatus 10 from coming into contact with the user or other surfaces.

In operation, when switch 130 is turned "on" the voltage regulator supplies power to the capillary to be 90, which causes the capillary tube to be heated. Also, when switch 130 is turned "on" the valve 80 is opened such that solution 30 flows from reservoir 20 into the capillary tube 90 where it vaporizes as it passes through the capillary tube. The cyanoacrylate vapor as it emerges from the capillary tube can be directed at the area to be tested and as the vapor comes into contact with latent fingerprint residue the cyanoacrylate polymerizes to expose an image of the print.

When switch 130 is closed, valve 80 closes and the supply of power to the capillary tube is turned off. Thus, when switch 130 is closed, solution flow through the capillary tube is stopped and the capillary tube is allowed to cool.

The reservoir can be of any suitable volume, such as from 2 to 10 ml, though it will be appreciated that larger volumes may be desirable for certain applications. Preferably the reservoir is a replaceable cartridge with a seal at one end and which is punctured to allow flow of liquid into the valve 80 when the cartridge is inserted into a mating receptacle in the housing 140. The capillary tube can be any suitable size and dimensions. The inner diameter of the capillary tube can be from between about 0.004 to 0.010 inches and the outer diameter of the capillary tube can be from between about 0.008 to 0.02 inches. For example, the capillary tube can be about 40 mm long and have inner and outer diameters of about 0.006 inches and 0.012 inches, respectively. The capillary tube can have a diameter of 0.01 and to 10 mm, preferably 0.05 to 1 mm, and more preferably 0.1 to 0.5 mm and a preferred length of 50 to 200 times the width to provide a flow passage of capillary size. Alternatively, the capillary passage can be of circular or non-circular cross section and defined by a transverse cross sectional area of the passage which can be $8 \times 10^{-5}$ to 80 $mm^2$, preferably $2 \times 10^{-3}$ to $8 \times 10^{-1}$ $mm^2$ and more preferably $8 \times 10^{-3}$ to $2 \times 10^{-1}$ $mm^2$.

The liquid flow rate of the cyanoacrylate solution through valve 80 and the capillary tube 90 is controlled by the viscosity of the solution, the force of the spring 50 and the inner diameter of the capillary tube. Preferably, the solution flow rate can be from between about 1 µl/sec to 10 µl/sec. Thus, by way of example, for a solution flow rate of 2 µl/sec, a 2 ml reservoir can hold sufficient solution for approximately 17 minutes of operation.

The directed vapor that exits the capillary tube can afford an efficient use of the consumable cyanoacrylate solution. Furthermore, latent fingerprints that come into contact with the vaporized solution become visible to the eye in a very short time. Latent fingerprints are preferably visible in as little time as 10-15 seconds. The visible fingerprints can either be photographed directly or lifted after application of powder. Thus, the apparatus and method of the invention can provide an economically efficient way to detect latent fingerprints.

A preferred cyanoacrylate solution comprises a mixture of liquid cyanoacrylate monomer and a suitable solvent stored in the reservoir. A solvent such as propylene carbonate prevents the cyanoacrylate from solidifying or polymerizing in the liquid phase. Liquid phase storage of the cyanoacrylate is convenient and capillary tube vaporization of cyanoacrylate can produce an efficient vapor that is directed at the area to be tested. Furthermore, unlike pure cyanoacrylate, the mixture of the invention does not bond to skin, which can make it easier to use.

The preferred monomers are cyanoacrylate esters and many are commercially available as "instant" adhesives, e.g. Loctite® Product 420, which is a low viscosity ethyl cyanoacrylate adhesive. The cyanoacrylate monomers have the general formula: $CH_2=C(CN)(COOR_1)$ wherein $R_1$ represents a hydrocarbyl or substituted hydrocarbyl group such as a straight chain or branched chain alkyl group having 1 to 12 carbon atoms (which may be substituted with a halogen atom or an alkoxy group), a straight chain or branched chain alkene group having 2 to 12 carbon atoms, a straight chain or branched chain alkyne group having 2 to 12 carbon atoms, a cycloalkyl group, or an aryl group.

The cyanoacrylate vapors are most suitably generated from the monomers. This may be done at ambient pressure. Cyanoacrylate ester monomers are preferred because of their ready availability, better known handling properties and low depolymerization temperatures.

The cyanoacrylate esters used in the invention can be any suitable monomer such as methyl 2-cyanoacrylate; ethyl 2-cyanoacrylate; propyl 2-cyanoacrylate; butyl 2-cyanoacrylate; allyl 2-cyanoacrylate; methoxyethyl 2-cyanoacrylate; ethoxyethyl 2-cyanoacrylate; 2-chloroethyl 2-cyanoacrylate; cyclohexyl 2-cyanoacrylate; ethoxycarbonylmethyl 2-cyanoacrylate; and trifluoroethyl 2-cyanoacrylate.

In addition to propylene carbonate, other suitable solvents can be used, such as dimethyl carbonate; diethyl carbonate; ethylene carbonate; diphenyl carbonate; diethylene glycol bis(allyl carbonate); 1,3 propanediol bis(allyl carbonate); 1,4 butanediol bis(allyl carbonate); triethylene glycol bis (allyl carbonate); trichloroethylene; and acetone. The cyanoacrylate solution can contain from between about 1 and 20% by volume, preferably 5 to 15%, and most preferably 10% cyanoacrylate, with the balance solvent.

It will be appreciated by those skilled in the art that the development of latent fingerprints can be accelerated by directing an increased amount of the cyanoacrylate vapor at the target area. By using the apparatus of the invention, the development of latent prints can take as little time as 5 to 25 seconds. The apparatus of the invention provides an economical, safe, convenient and portable means of detecting latent fingerprints.

According to a further embodiment, a soluble fluorescent dye can be added to the cyanoacrylate solution. Thus, the apparatus of the invention can generate fluorescent vapor. When latent fingerprints are developed using the fluorescent cyanoacrylate vapor, they can be rendered visible by subsequent exposure to an ultraviolet light source.

The fingerprint detection method can be used to create very good quality fingerprint images on substantially nonporous surfaces like metal, glass and plastic; and satisfactory fingerprint images can be created on porous surfaces.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A method of using a fingerprint detection apparatus comprising:
   providing the fingerprint detection apparatus, the apparatus comprising a liquid source containing a solution which upon vaporization and contact with a surface to be inspected can provide an image of a fingerprint;
   a flow passage in fluid communication with the liquid source;
   a valve operable to control flow of liquid from the liquid source to the flow passage;
   a heater arranged to heat the solution in the flow passage into a gaseous state; and
   a switch operable to activate the valve and the heater such that solution flowing through the flow passage is vaporized and directed outwardly from the apparatus, the method further comprising flowing the solution through the flow passage while heating the flow passage with the heater, forming a vapor by vaporizing the solution, directing the vapor onto the surface to be inspected, and inspecting said surface so as to locate fingerprints.

2. The method of claim 1, wherein the solution comprises a cyanoacrylate solution.

3. The method of claim 2, wherein the cyanoacrylate solution comprises a mixture of cyanoacrylate monomer and a solvent.

4. The method of claim 3, wherein the cyanoacrylate solution comprises 1 to 20% by volume of the cyanoacrylate monomer.

5. The method of claim 1, further comprising replacing the liquid source with a replaceable cartridge containing a cyanoacrylate solution.

6. The method of claim 1, wherein the solution is supplied to the flow passage by pressurizing the liquid source.

7. The method of claim 1, further comprising forming an image of a latent fingerprint by reacting the vapor with organic compounds of the fingerprint.

8. The method of claim 1, wherein the solution includes a soluble fluorescent dye and the method includes generating a fluorescent vapor which is directed at the surface to be inspected.

9. The method of claim 1, wherein the apparatus is a portable hand held apparatus and the method includes holding the apparatus in a user's hand while directing the vapor at the surface to be inspected.

10. The method of claim 1, wherein the flow passage is a capillary sized passage having a maximum width of 0.01 to 10 mm or transverse area of $8 \times 10^{-5}$ to 80 mm$^2$.

11. A method of using a fingerprint detection apparatus comprising:
    providing the fingerprint detection apparatus, the apparatus comprising a liquid source containing a solution which upon vaporization and contact with a surface to be inspected can provide an image of a fingerprint;
    a flow passage in fluid communication with the liquid source;
    a valve operable to control flow of liquid from the liquid source to the flow passage;
    a heater arranged to heat the solution in the flow passage into a gaseous state; and
    a switch operable to activate the valve and the heater such that solution flowing through the flow passage is vaporized and directed outwardly from the apparatus, the method further comprising pressing the switch to open the valve and activate the heater, flowing the solution through the flow passage while heating the flow passage with the heater, forming a vapor by vaporizing the solution, directing the vapor onto the surface to be inspected, and inspecting said surface so as to locate fingerprints.

12. A fingerprint detection apparatus, comprising:
    a liquid source containing a solution which upon vaporization and contact with a surface to be inspected can provide an image of a fingerprint;
    a flow passage in fluid communication with the liquid source;
    a valve operable to control flow of liquid from the liquid source to the flow passage;
    a heater arranged to heat the solution in the flow passage into a gaseous state; and
    a switch operable to activate the valve and the heater such that solution flowing through the flow passage is vaporized and directed outwardly from the apparatus,
    wherein the switch is operable to open the valve and connect a power supply to the heater.

13. The fingerprint detection apparatus of claim 12, wherein the flow passage comprises a capillary tube having a maximum diameter of 0.01 to 10 mm.

14. The fingerprint detection apparatus of claim 13, wherein the capillary tube comprises a metal tube and the heater comprises a section of the capillary tube which is heated by resistance heating thereof.

15. The fingerprint detection apparatus of claim 12, wherein the apparatus includes a receptacle receiving the liquid source and the liquid source is a replaceable cartridge.

16. The fingerprint detection apparatus of claim 12, wherein liquid source includes a spring biased plunger operable to force liquid out of the liquid source.

17. The fingerprint detection apparatus of claim 12, wherein the heater comprises a layer of resistance heating material located along the flow passage.

18. The fingerprint detection apparatus of claim 12, wherein the solution comprises a cyanoacrylate solution.

19. A fingerprint detection apparatus, comprising:
    a liquid source containing a solution which upon vaporization and contact with a surface to be inspected can provide an image of a fingerprint;
    a flow passage in fluid communication with the liquid source;
    a valve operable to control flow of liquid from the liquid source to the flow passage;
    a heater arranged to heat the solution in the flow passage into a gaseous state; and
    a switch operable to activate the valve and the heater such that solution flowing through the flow passage is vaporized and directed outwardly from the apparatus,
    wherein the switch is operable to open the valve and connect a power supply to the heater, and, wherein the power supply comprises at least one battery and a voltage regulator, the voltage regulator being operable to supply a selected voltage to the heater.

* * * * *